United States Patent [19]

Bouyssou et al.

[11] Patent Number: 5,804,589
[45] Date of Patent: Sep. 8, 1998

[54] USE OF N-CYCLOHEXYL BENZAMIDES FOR TREATING BOWEL DISORDERS

[75] Inventors: Thierry Bouyssou, Plaisir; Hèlène Christinaki, Meudon; Alain Renaud, Rueil Malmaison, all of France

[73] Assignee: Laboratoires Jacques Logeais, Issy-les-Moulineaux Cedex, France

[21] Appl. No.: 945,853

[22] PCT Filed: Jun. 21, 1996

[86] PCT No.: PCT/FR96/00976

§ 371 Date: Nov. 7, 1997

§ 102(e) Date: Nov. 7, 1997

[87] PCT Pub. No.: WO97/00680

PCT Pub. Date: Jan. 9, 1997

[30] Foreign Application Priority Data

Jun. 23, 1995 [FR] France ................................. 95 07606

[51] Int. Cl.[6] .............................................. A61K 31/445
[52] U.S. Cl. .......................... 514/331; 514/327; 514/317
[58] Field of Search .................................. 514/331, 327, 514/317

[56] References Cited

U.S. PATENT DOCUMENTS 5,273,973  12/1993  Christinaki et al. ............... 514/331

FOREIGN PATENT DOCUMENTS 0 507 672  10/1992  European Pat. Off. .

OTHER PUBLICATIONS by N.W. Read et al., "The Importance of 5-Hydroxytryptamine Receptors in the Gut", *Pharmac. Ther.*, vol. 62, No. 1-2, 1994, pp. 159-173.

by N.J. Talley, "5-Hydroxytryptamine agonists and antagonists in the modulation of gastrointestinal motility and sensation: clinical implications", *Aliment. Pharmacol. Ther.*, vol. 6, No. 3, 1992, pp. 273-279.

*Primary Examiner*—William R. A. Jarvis
*Attorney, Agent, or Firm*—Young & Thompson

[57] ABSTRACT

The present invention relates to the use of the compounds of formula:

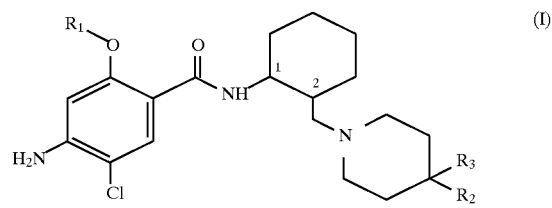

in which $R_1$ is a linear, branched or cyclized $C_1$–$C_5$ alkyl radical and $R_2$ represents a hydrogen atom, a linear or branched $C_1$–$C_5$ alkyl radical, a hydroxyl radical, a $C_1$–$C_5$ alkoxy radical or a $C_1$–$C_2$ hydroxyalkyl radical, and $R_3$ represents a hydrogen atom or $R_2$ and $R_3$ both represent a $C_1$–$C_5$ alkyl radical, these compounds being 2R in configuration, as well as of the racemates comprising these compounds, and of their pharmaceutically acceptable salts, for the manufacture of a medicament intended for the treatment of pain of visceral origin.

6 Claims, No Drawings

USE OF N-CYCLOHEXYL BENZAMIDES FOR TREATING BOWEL DISORDERS

This application is a 371 of PCT/FR96/00976, filed Jun. 21, 1996.

The present invention relates to new therapeutical applications of N-cyclohexylbenzamides.

Irritable bowel syndrome (IBS) is defined by the presence of abdominal pain, of irregular defecation, which may or may not be associated with the abdominal pain, and generally of abdominal distensions.

The multiplicity of these symptoms has led to the proposal of a classification of this pathology as a function of the existence of constipation or of diarrhoea.

The constipation observed in certain forms of IBS can be treated by agents which stimulate intestinal motoricity and more particularly colic motoricity.

The N-cyclohexylbenzamides described in EP 0,507,672 are known to stimulate digestive motoricity and can therefore be proposed for restoring colic transit in patients affected by IBS where constipation is predominant.

It has been shown that, in this pathology, patients complaining of abdominal pain exhibit a lowered visceral sensitivity threshold (Médecine/Sciences (1994), 10, 1107–15).

This threshold can be raised by various pharmacological agents such as kappa agonists or certain 5-$HT_3$ antagonists, such as granisetron (WO 94/01095). The latter compound is, moreover, known to decrease rectal motoricity (Aliment. Pharmacol. Ther. (1993), 7, 175–80) and other 5-$HT_3$ antagonists, such as ondansetron (Dig. Dis. Sci. (1990), 35, 477–80), are known to slow down colic transit.

The N-cyclohexylbenzamides described in EP 0,507,672, in contrast to compounds such as granisetron, do not possess an effect with respect to 5-$HT_3$ receptors.

The Applicant Company has now discovered that certain compounds described in EP 0,507,672 have the property of increasing the threshold for perception of pain of visceral origin.

The Applicant Company has also discovered that these same compounds possess an anti-inflammatory effect with respect to a model for ulcerative colitis.

These compounds correspond to the general formula

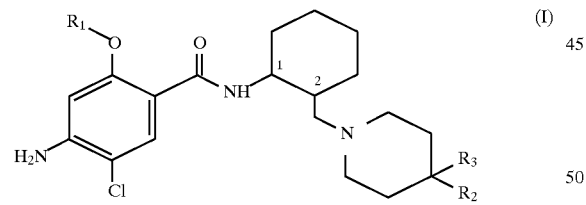

in which $R_1$ is a linear, branched or cyclized $C_1$–$C_5$ alkyl radical and $R_2$ represents a hydrogen atom, a linear or branched $C_1$–$C_5$ alkyl radical, a hydroxyl radical, a $C_1$–$C_5$ alkoxy radical or a $C_1$–$C_2$ hydroxyalkyl radical, and $R_3$ represents a hydrogen atom or $R_2$ and $R_3$ both represent a $C_1$–$C_5$ alkyl radical.

The presence of two asymmetric centres means that the formula I encompasses four stereoisomers. The compounds used in the invention have the 2R absolute configuration, the preferred compounds having the 1R, 2R absolute configuration. The racemic compounds with the cis relative configuration (which are equimolar mixtures of the 1R, 2R and 1S, 2S enantiomers) contain the active isomer and can therefore be used in the invention. Likewise, the racemic compounds with the trans relative configuration (which are equimolar mixtures of the 1S, 2R and 1R, 2S enantiomers) can also be used in the invention.

The particularly preferred compounds are those corresponding to the formula I where $R_1$ is a methyl or cyclopropylmethyl radical, $R_2$ is a methyl radical and $R_3$ is a hydrogen atom.

The compounds of formula I can be prepared by synthetic methods described in EP 0,507,672, by condensing the benzoic acids of the general formula II with the diamines of general formula III exhibiting the desired stereochemistry

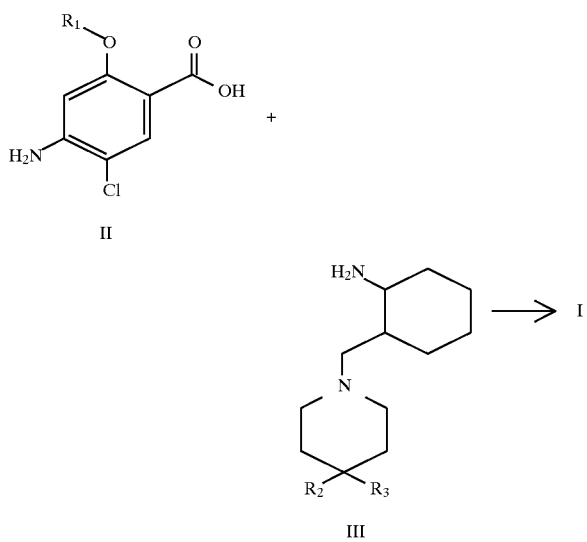

The racemic diamines III with the cis relative configuration are prepared, according to the synthetic route described in EP 0,507,672, from (cis)-2-(trifluoroacetamido)cyclohexanecarboxylic acid.

The diamine III where $R_2$=H and $R_3$=$CH_3$, with 1R, 2R absolute configuration, has also been described in EP 0,507,672.

The diamine III where $R_2$=H and $R_3$=$CH_3$, with 1S, 2R absolute configuration, has been prepared from the amino ester IV (itself obtained according to the method described in Tetrahedron Letters (1984), 25, 2557–2560) according to the following series of reactions:

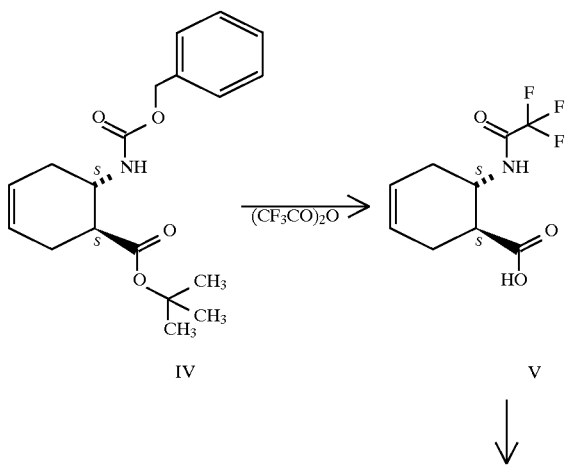

-continued

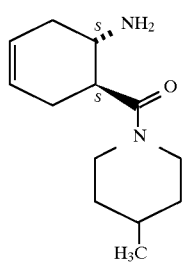

VII

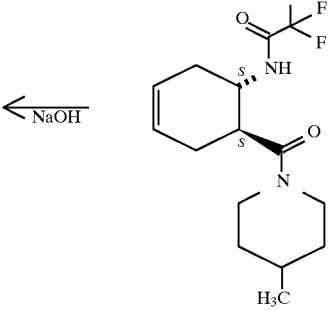

VI

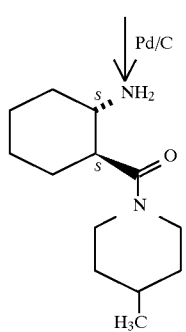

VIII

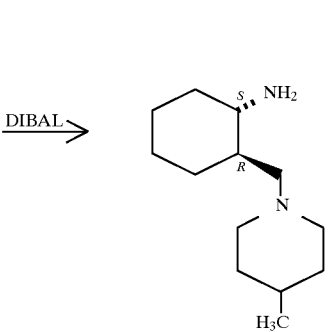

IX

The subject of the present invention is therefore the use of the compounds of formula I or of their pharmaceutically acceptable salts for the manufacture of a medicament intended for the treatment of pain of visceral origin, in particular present in patients affected by IBS.

Another subject of the present invention is the use of the compounds of formula I or of their pharmaceutically acceptable salts for the manufacture of a medicament intended for the treatment of inflammatory colites such as haemorrhagic rectocolites or Crohn's disease.

The posologies in man, by oral administration, are from approximately 1 mg to approximately 200 mg per day.

The results obtained, with respect to the tests which demonstrate the pharmacological properties which have just been stated, are given below.

I—Activity with Respect to 5-$HT_3$ Receptors

1) Affinity with respect to receptors

The affinity of the compounds for 5-$HT_3$ receptors was measured according to the method described in Bioch. Pharmacol. (1990), 40, (7), 1541–1550, by using membrane preparations of NG 108–15 cells and tritiated BRL 43694 as specific ligand.

The compounds of formula I show low affinities, greater than micromolar, for 5-$HT_3$ receptors. By way of comparison, the Ki of ondansetron is 16 nM.

2) Bezold-Jarisch reflex

The 5-$HT_3$ antagonist activity of products was evaluated in vivo by measuring their property of inhibiting a bradycardia induced by serotonin, according to the method described in J. Pharm. & Exp. Therap. (1989), 248, 197–201.

None of the compounds of formula I antagonises bradycardia up to doses of 1 mg·kg i.v. By way of comparison, ondansetron antagonises bradycardia with an $IC_{50}$ of approximately 0.003 mg/kg i.v.

II—Visceral Sensitivity

The first model consists in observing, in the rat, the abdominal contractures produced by a rectal distension applied to a mucous membrane which has been irritated beforehand. The number of contractures is proportional to the intensity of the pain experienced. A similar model has been described in Neurogastroenterol. and Mot. (1994), 6, 140, where it is shown that the products which decrease the perception of pain in man decrease the number of contractures observed in the rat.

Procedure

Male Sprague-Dawley rats weighing 180 g are deprived of food for 12 hours. Under slight fluothane anaesthesia, an intrarectal probe is introduced (5 cm from the anus) and 1.5 ml of 1% dilute acetic acid are injected. The acid immediately flows out via the anus. This rapid contact of the acid makes it possible to irritate the mucous membrane (model for rectal colitis). 1 h 30 after irritation, a small latex balloon (diameter when empty 2 mm, length 1 cm), mounted on a polyurethane catheter (int. diameter 1 mm), is introduced into the rectum (5 cm from the anus) under slight fluothane anaesthesia. The catheter is attached to the base of the tail with adhesive tape and protected by a glass tube. The test product is administered by force feeding and the rat is then introduced into a crystallizing dish covered with a grid. The free ends of the tube and of the catheter are passed through the grid in order to carry out the dilations.

A distension is carried out 2 h 30 after irritating the rectum. The small balloon is dilated with 1.5 ml of distilled water (intracolic pressure equal to 60 mm Hg on average). Dilation is maintained for 10 minutes, during which the abdominal contractures are counted. The small balloon is then deflated by sucking off the distilled water.

Results

They are expressed by the mean number of contractures observed with respect to five rats for the 10 minutes during which they are subjected to a distension.

| Compound No. | $R_1$ | $R_2$ | $R_3$ | Salt | Configuration | Dose mg/kg p.o. | No. of contractures ± standard deviation |
|---|---|---|---|---|---|---|---|
| placebo | | | | | | | 23.8 ± 1.6 |
| 1 | $CH_3$ | $CH_3$ | H | HCl | R, R | 0.3 | 3.4 ± 2.1* |
| 2 | $CH_3$ | OH | H | HCl | cis | 0.3 | 9.2 ± 5.3* |
| 3 | $CH_3$ | $CH_2OH$ | H | HCl | cis | 0.3 | 13.2 ± 2.4* |
| 4 | $CH_3$ | $(CH_3)_2$ | $CH_3$ | HCl | cis | 0.3 | 10.6 ± 4.2* |
| 5 | $CH_3$ | $C-(CH_3)_3$ | H | HCl | cis | 0.3 | 10.6 ± 3.8* |

-continued

| Compound No. | R₁ | R₂ | R₃ | Salt | Configuration | Dose mg/kg p.o. | No. of contractures ± standard deviation |
|---|---|---|---|---|---|---|---|
| 6 | (cyclopropyl) | $CH_3$ | H | base | R, R | 0.1<br>0.3<br>1 | 3.3 ± 1.9*<br>7.3 ± 2.6*<br>9.4 ± 4.2* |
| 7 | —CH(CH₃)₂ | $CH_3$ | H | HCl | cis | 0.3 | 7.6 ± 0.5* |
| 8 | (cyclopentyl) | $CH_3$ | H | base | R, R | 0.3 | 9.2 ± 1.3* |
| 9 | (cyclopropyl) | $CH_3$ | H | base | 1S, 2R | 0.3 | 6.3 ± 3.5* |

*significantly different from the placebo at $p < 0.05$ (Dunett test).

III—Anti-inflammatory Activity

A model for ulcerative colitis induced in the rat by an intracolic instillation of trinitrobenzenesulphonic acid has already been described, for example in Gut (1992), 33, 1498–1503.

The beneficial effect of a treatment on the development of this colitis can be evaluated, on the one hand, by the overall state of health of the animal, represented for example by the change in weight, and, on the other hand, by a histological study of the colon at the end of the experiment.

Procedure

Male Sprague-Dawley rats (140–150 g), deprived of food since the previous day, are subjected, under general anaesthesia (isoflurane), to irritation of the mucous membrane of the distal colon (7 cm from the anus) with 1 ml of a 50 mg/ml aqueous trinitrobenzenesulphonic acid (TNB) solution. On the following day, the rats are randomized in two equal-sized groups (n=7) which then receive the treatment (placebo or product) by forcefeeding, mornings and evenings. The products are administered at 1 mg/kg p.o. twice daily.

The treatment is administered for the ten days which follow irritation of the colon. The animals are weighed every morning from D5 to D10. The animals are deprived of food on D9 and humanely killed on D10. The colons are removed and macroscopically and then histologically examined.

Results

The results obtained with Compound 6 are given by way of information.

Change in weight

| Number of days after treatment with TNB | Mean weight of the animals | |
|---|---|---|
| | treated with the placebo | treated with Compound 6 |
| 5 | 130 ± 8 | 153 ± 15 |
| 6 | 139 ± 18 | 177 ± 23* |
| 7 | 142 ± 20 | 186 ± 27* |
| 8 | 147 ± 23 | 194 ± 34* |
| 9 | 158 ± 30 | 206 ± 39* |

*significantly different from the placebo at $p < 0.05$ (Dunett test)

Macroscopic analysis of the colons

The macroscopic appearance of the colons was graded as follows:

Stages
  0: no trace of irritation
  1: slightly vasodilated mucous membrane
  2: vasodilated mucous membrane and adhesions
  3: haemorrhagic and sclerotic mucous membrane and adhesions
  4: ulcerated and haemorrhagic mucous membrane and adhesions.

The results are combined in the table below and represent the number of animals exhibiting the various stages.

| Stages | Number of animals treated with the placebo | Number of animals treated with Compound 6 |
|---|---|---|
| 0 | 0 | 0 |
| 1 | 0 | 1 |
| 2 | 0 | 4 |
| 3 | 3 | 2 |
| 4 | 3 | 0 |

The seriousness of the lesions is significantly greater with the placebo than with Compound 6 at $p>0.05$. The statistical calculation was carried out by a chi-squared test, the class of Stages 1 and 2 (size 0 treated with the placebo, 5 treated with the product) being compared with the class of Stages 3 and 4 (size 6 treated with the placebo, 2 treated with the product).

Histological analysis

Sections of the colon are fixed with formaldehyde and enclosed in paraffin blocks. 5 μm sections are prepared, stained with haemalum-eosin and evaluated by optical microscopy according to the following gradings:

Stages
  0: absence of inflammatory cells
  1: a few inflammatory cells are present
  2: large number of inflammatory cells
  3: massive presence of inflammatory cells with increase in the thickness of the layer concerned without architectural distortion
  4: massive presence of inflammatory cells with increase in the thickness of the layer concerned and architectural distortion. (loss of the normal architectural appearance)

The colon was divided into three mucous, submucous and muscular layers and each layer was graded according to the preceding criteria.

The sum of the gradings attributed to each substructure defines, per animal, an index which takes into account both the afflux of the inflammatory cells and the architectural distortion.

|  | Number of animals | Index |
|---|---|---|
| Placebo | 3 | 12 |
|  | 1 | 7 |
|  | 2 | 6 |
| Compound 6 | 2 | 11 |
|  | 3 | 3 |
|  | 1 | 1 |
|  | 1 | 0 |

A statistical calculation was carried out by a chi-squared test, the class combining the indices 0 to 5 (size 0 treated with the placebo, 5 treated with the product) being compared with the class combining the indices 6 to 12 (size 6 treated with the placebo, 2 treated with the product). The inflammatory state is significantly more serious treated with the placebo than treated with Compound 6.

Treatment with Compound 6 thus shows, in this model, that, with respect to the placebo, the rats exhibit a significantly improved change in weight and that the lesional appearance of the colon is less serious, this improvement being correlated with a decrease in the afflux of the inflammatory cells.

Examples of the preparation of the compounds of formula I will be given below.

Compound 3

4-Amino-5-chloro-2-methoxybenzoic acid (2.92 g) and N,N-carbonyldiimidazole (2.35 g) are dissolved in 80 ml of THF. After stirring for one hour at room temperature, 2-(4-hydroxypiperidinomethyl)cyclohexylamine (B.p.: 160° C./0.5 mm Hg) (3.45 g) is added to the reaction mixture. After stirring for 20 h, the solvent is evaporated and the residue is taken up in water and acidified to pH 5. The aqueous phase is extracted with ethyl acetate, basified to pH 10 and then again extracted with ethyl acetate. The final organic phase is dried over sodium sulphate, filtered and then evaporated under vacuum. The residue obtained is treated with a solution of hydrochloric acid in ether and the hydrochloride thus obtained is crystallized from water and then collected by filtration.

Melting point: 145°–216° C. (dec.); IR (C=O): 1635 cm$^{-1}$ (KBr).

Compound 8

Compound 8 is obtained according to the above procedure from 4-amino-5-chloro-2-(cyclopentyloxy)benzoic acid and (1R,2R)-2-(4-methylpiperidinomethyl)cyclohexylamine. The base is purified by chromatography on silica (eluent $CH_2Cl_2/CH_3CO_2C_2H_5/CH_3OH$; 80/15/5) and then crystallized from water.

Melting point: 173°–175° C.; IR (C=O): 1634 cm$^{-1}$ ($CHCl_3$) $[a]_D$=−52.6° (c=1, $CH_3OH$). T=20° C.

Compound 9

Compound 9 is obtained in an identical way from 4-amino-5-chloro-2-(cyclopropylmethoxy)benzoic acid and from (1S,2R)-2-(4-methylpiperidinomethyl)cyclohexylamine. The benzamide obtained is purified in the base form by chromatography on silica (eluent: $CH_2Cl_2/CH_3CO_2C_2H_5/CH_3OH$; 80/15/5) and crystallized from ethyl ether.

Melting point: 145°–147° C.; IR (C=O): 1635 cm$^{-1}$ ($CHCl_3$) $[a]_D$=+68.1° (c=1, $CH_3OH$). T=20° C.

(1S,2S)-2-Trifluoroacetamido-4-cyclohexenecarboxylic acid (V)

The amino ester IV (6.4 g) is treated with trifluoroacetic anhydride (17.6 ml) for 5 days. The reaction mixture is evaporated under vacuum and the residue is taken up in a 5% aqueous $NaHCO_3$ solution. The aqueous phase is extracted with ethyl acetate, acidified and then extracted with ethyl acetate. The final organic phase is dried over sodium sulphate and the solvent is then evaporated under vacuum to provide 2.4 g of the product V.

[IR (C=O)=1705 cm$^{-1}$ (KBr)].

(1S,2S)-1-Trifluoroacetamido-2-(4-methyl-piperidino) carbonyl-4-cyclohexene (VI)

The compound obtained in the preceding stage (0.2 g), used without additional purification, and carbonyldiimidazole (0.137 g) are dissolved in THF (5 ml). After stirring for 2 h 30, 4-methylpiperidine (0.084 g) is added and the reaction mixture is left for 24 h. The solvent is evaporated under reduced pressure and the residue taken up in dichloromethane. The organic phase is washed with a saturated aqueous $NaHCO_3$ solution, dried over $Na_2SO_4$ and evaporated under vacuum. The residue is crystallized from petroleum ether to provide 100 mg of the expected product.

Melting point: 169°–170° C.; IR(C=O): 1721, 1623 cm$^{-1}$ ($CHCl_3$) $[a]_D$=−9.9° (c=1, $CH_3OH$). T=20° C.

(1S,2S)-1-Amino-2-(4-methylpiperidino)carbonyl-4-cyclohexene (VII)

The product obtained in the preceding stage (1.3 g) is dissolved in ethanol (30 ml) and then treated with an aqueous solution of sodium hydroxide (0.33 g in 10 ml of water) at reflux for 7 hours. After neutralizing the reaction mixture with 1N HCl, the solvents are driven off under vacuum. The residue is taken up in 2N HCl and the aqueous phase is extracted with ethyl ether, basified to pH 10 with 2N NaOH and extracted with ethyl acetate. The organic phase is dried over $Na_2SO_4$ and evaporated under vacuum. The product (0.63 g) is obtained in the form of an oil and used without additional purification.

(1S,2R)-2-(4-methlylpiperidinocarbonyl) cyclohexylamine (VIII)

The cyclohexene VI (0.57 g) is dissolved in methanol (50 ml) in the presence of 10% Pd/C (50 mg) and of 3N HCl (0.85 ml). The reaction mixture is stirred under a slight hydrogen pressure for 20 h. The catalyst is removed by filtration and the solvent is driven off under vacuum. The residue is taken up in a saturated $K_2CO_3$ solution and the aqueous phase is extracted with ethyl acetate. The organic phase is dried over $Na_2SO_4$ and then evaporated under vacuum to provide the reduced derivative VIII (0.46 g) in the form of an oil.

$[\alpha]_D$=+82.8° (c=1, $CH_3OH$). T=20° C. IR (C=O): 1616 cm$^{-1}$ ($CHCl_3$).

(1S,2R)-2-(4-methylpiperidinomethyl)cyclohexylamine (IX)

The amide derivative VIII (0.42 g) is dissolved in 10 ml of toluene and then treated at −60° C. with diisobutylaluminium hydride (9.4 ml of a 1M solution in toluene) for 8 hours. The reaction mixture is hydrolysed by addition of 2N HCl. The aqueous phase is separated from the toluene, washed with chloroform, rendered alkaline by addition of 2N NaOR and then extracted with chloroform. The organic phase is dried over $Na_2SO_4$ and then evaporated under vacuum to provide the diamine (0.25 g).

$[\alpha]_D$=−12.1° (C=1, $CH_3OH$). T=20° C.

We claim:

1. A method for the treatment of pain of visceral origin which comprises administering to a patient in need thereof a therapeutically effective amount of a compound selected from the compounds of formula:

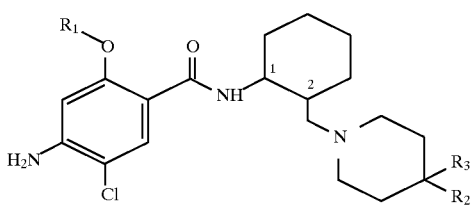

in which
- $R_1$ is a linear, branched or cyclized $C_1$–$C_5$ alkyl radical and
- $R_2$ represents a hydrogen atom, a linear or branched $C_1$–$C_5$ alkyl radical, a hydroxyl radical, a $C_1$–$C_5$ alkoxy radical or a $C_1$–$C_2$ hydroxyalkyl radical, and
- $R_3$ represents a hydrogen atom
- or $R_2$ and $R_3$ both represent a $C_1$–$C_5$ alkyl radical, these compounds being 2R in configuration, as well as of the racemates comprising these compounds, and their pharmaceutically acceptable salts.

2. A method as claimed in claim 1, in which a compound of formula I with the 1R,2R configuration is administered.

3. A method as claimed in claim 1, in which a compound of formula I in which $R_1$ is a methyl or cyclopropylmethyl radical, $R_2$ is a methyl radical and $R_3$ is a hydrogen atom is administered.

4. A method for the treatment of inflammatory colitis which comprises administering to a patient in need thereof a therapeutically effective amount of a compound selected from the compounds of formula:

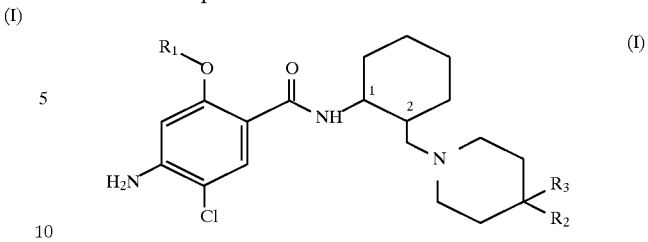

in which
- $R_1$ is a linear, branched or cyclized $C_1$–$C_5$ alkyl radical and
- $R_2$ represents a hydrogen atom, a linear or branched $C_1$–$C_5$ alkyl radical, a hydroxyl radical, a $C_1$–$C_5$ alkoxy radical or a $C_1$–$C_2$ hydroxyalkyl radical, and
- $R_3$ represents a hydrogen atom
- or $R_2$ and $R_3$ both represent a $C_1$–$C_5$ alkyl radical, these compounds being 2R in configuration, as well as of the racemates comprising these compounds, and their pharmaceutically acceptable salts.

5. A method as claimed in claim 4, in which a compound of formula I with the 1R,2R configuration is administered.

6. A method as claimed in claim 4, in which a compound of formula I in which $R_1$ is a methyl or cyclopropylmethyl radical, $R_2$ is a methyl radical and $R_3$ is a hydrogen atom is administered.

* * * * *